(12) United States Patent
Barluenga Mur et al.

(10) Patent No.: US 7,521,458 B2
(45) Date of Patent: Apr. 21, 2009

(54) SPIROPIPERIDYLRIFAMYCINS FOR THE TREATMENT OF MYCOBACTERIAL INFECTIONS

(75) Inventors: José Barluenga Mur, Oviedo (ES);
Fernando Aznar Gómez, Oviedo (ES);
Maria Paz Cabal Naves, Oviedo (ES);
Ana Belén Garcia Delgado, Giión (ES);
Carlos Valdés Gómez, Llanera (ES)

(73) Assignee: Universidad de Oviedo, Oviedo (Asturias) (ES)

( * ) Notice: Subject to any disclaimer, the term of this patent is extended or adjusted under 35 U.S.C. 154(b) by 37 days.

(21) Appl. No.: 11/572,416

(22) PCT Filed: Jul. 4, 2005

(86) PCT No.: PCT/ES2005/000380

§ 371 (c)(1),
(2), (4) Date: Jan. 19, 2007

(87) PCT Pub. No.: WO2006/027397

PCT Pub. Date: Mar. 16, 2006

(65) Prior Publication Data

US 2007/0225266 A1    Sep. 27, 2007

(30) Foreign Application Priority Data

Jul. 19, 2004 (ES) .............................. P200401767

(51) Int. Cl.
C07D 491/20 (2006.01)
A61K 31/438 (2006.01)
A61P 31/04 (2006.01)

(52) U.S. Cl. ...................... 514/278; 540/456
(58) Field of Classification Search ................. 540/456; 514/278
See application file for complete search history.

(56) References Cited

U.S. PATENT DOCUMENTS 4,219,478 A    8/1980    Marsili

OTHER PUBLICATIONS

Rubio, E. y col. NMR spectroscopic analysis of new spiropiperidylrifamycins. Magnetic Resonance in Chemistry. Apr. 2005, vol. 43, No. 4, pp. 269-282.

Informe de Busqueda Internacional (PCT International Search Report) for PCT/ES2005/000380, issued Sep. 28, 2005, inbcluding Opinion Escrita (PCT Written Opinion) issued Sep. 28, 2005.

*Primary Examiner*—Bruck Kifle
(74) *Attorney, Agent, or Firm*—Peter B. Scull; Kristina M. Kalan; Berenbaum, Weinshienk & Eason

(57) ABSTRACT

The compounds of formula (1), their pharmaceutically acceptable salts and their solvates, wherein $R^1$ is a radical selected between hydrogen and alkyl; $R^2$ is selected from hydroxyalkyl, phenyl, phenyl mono-substituted and phenyl di-substituted in positions 3 and 4; $R^3$ is selected from phenyl, phenyl mono-substituted and phenyl di-substituted in positions 3 and 4; the substituents of the phenyl of $R^2$ and $R^3$ selected from halogen, $(C_1-C_4)$-alkyl and $(C_1-C_4)$-alkoxyl and $R^4$ is selected from hydrogen, alkyl allyl and homoallyl, they are useful for the treatment of mycobacterial infections, in particular for the treatment of infections produced by *Mycobacterium tuberculosis*, *Mycobacterium avium-intracellulare* complex or *Mycobacterium kansasii*.

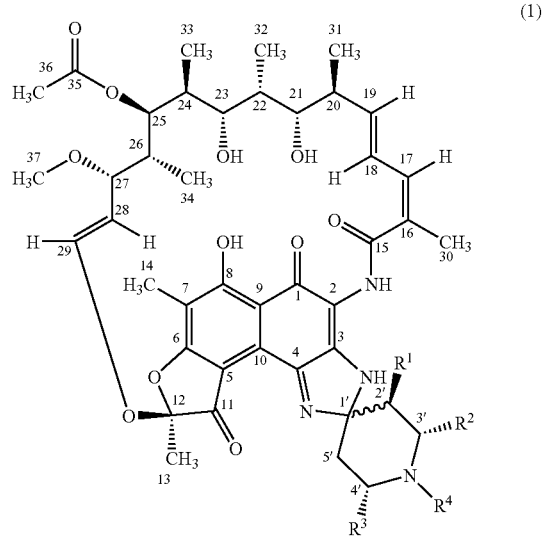

18 Claims, No Drawings

SPIROPIPERIDYLRIFAMYCINS FOR THE TREATMENT OF MYCOBACTERIAL INFECTIONS

CROSS REFERENCE TO RELATED APPLICATIONS

The present application is a 35 USC § 371 National Phase filing corresponding to PCT Application Number PCT/ES2005/00380, filed Jul. 4, 2005, which claims priority from the Spanish application no. P200401767, filed Jul. 19, 2004, both entitled "SPIROPIPERIDYLRIFAMYCINS FOR THE TREATMENT OF MYCOBACTERIAL INFECTIONS" the subject matter of which hereby being specifically incorporated herein by reference for all that is disclosed and taught therein.

This invention is related to new rifamycin derivatives from the spiropiperidylrifamycins family, which exhibit a high antibiotic activity, and also a procedure for their preparation.

BACKGROUND ART

Multiresistant tuberculosis is defined as that tuberculosis which is caused by strains of *Mycobacterium tuberculosis* resistant simultaneously to at least isoniazid and rifampicin. Its incidence has increased in the last number of years in an alarming rate in a numerous regions in the worldwide. The importance of this problem is illustrated in the decision taken by the WHO in 1994 to put into action a plan for the control and surveillance of multiresistant tuberculosis at a worldwide level (cfr. Guidelines for surveillance of drug resistance in tuberculosis WHO/TB/2003.320-WHO/CDS/RMD/2003.3). Among the strategies that have been developed against this serious problem which threatens worldwide health, is the development of new drugs to fight the types of strains involved.

Drugs for tuberculosis treatment are divided in "first line drugs" and "second line drugs". The first line is of greatest effectiveness, and plays an indispensable role in primary therapeutic regimes to guarantee the treatment of this disease. Only four drugs make up the first group, which are: isoniazid, rifampicin, pyrazinamide, and ethambutol. The rest of the drugs nowadays available are included within the category of "second line drugs".

For the treatment of multiresistant tuberculosis drug combinations are administered over prolonged periods of time. Nowadays, the choice treatment lasts six months and contemplates administration of a combination of isoniazid, rifampicin and pyrazinamide for two months, followed by the administration of isoniazid and rifampicin combination for four subsequent months. It is of vital importance to develop new drugs which permit reinforcement or improvement in the treatment of multiresistant tuberculosis.

On the other hand, related to the HIV epidemic and due to the generalized use in modern medicine of antitumour and immunosuppressor drugs, there have been increased infections produced by the named "atypical mycobacteria" (also known as "opportunist environmental mycobacteria" or as "nontuberculous mycobacteria"). This term includes numerous different species from whose method of transmission is not known, nor is their resistance mechanism to antimycobacterials. These atypical mycobacterias behave as microorganisms usually resistent to the drugs with antimycobaterial activity and pose a serious threat. From the numerous species isolated, *Mycobacterium avium-intracellulare* complex stands out for its frequency of producing serious disseminated infections and producing a pulmonar pathology undistinguishable from the one produced by *M. tuberculosis*. *Mycobacterium avium-intracellulare* complex behaves as multiresistant to the drugs of the "first" and "second line". In the therapeutic regimes the rifabutin is generally the elective treatment, associated to a macrolide and to a quinolone. The high toxicity in vivo of the rifabutin represents a common inconvenience. *Mycobacterium kansasii* usually has a pattern of sensitivity much more variable, even though it exhibits resistance to isoniazid and ethambutol.

Rifamycins are natural chemical substances that were isolated for first time in 1959 from cultures of *Nocardia Mediterranei* as a complex mix of rifamycins A-E (cfr. P. Sensi et al., *Il Fármaco, Ed. Sc.* 1959, vol. 14, pp. 146-147). They belong to the ansamycin family, antibiotics of great interest against Gram-positive bacteria and mycobacteria such as *M. tuberculosis*. They also have activity against the DNA-dependent bacterial RNA polymerase (cfr. C. Bartolucci et al., *Fármaco* 1992, vol. 47, p. 1367; C. Bartolucci et al., *Pharm. Pharmacol. Lett,* 1993, vol. 3, p. 1).

The structure of the rifamycins was determined by chemical degradation of the rifamycin S and by NMR spectroscopics studies. They present as common structural characteristic an aliphatic chain of 17 carbon atoms, called ansa, which connects two non adjacent positions of an aromatic plane chromophore core of naphtohydroquinone linked by an amide group.

The activity of these compounds is a consequence of the specific inhibition of the bacterial RNA polymerase through the formation of a very stable complex 1:1 between the drug and the enzyme, as it is shown in an investigation of the rifampicin. It has been proposed in a model in which the enzyme wraps the drug by the hydrophilic face and under the aromatic core, in such a way that the positions $C_3$ and $C_4$ do not participate in the joining. The studies of structure-activity relationship carried out with different rifamycins conclude that in order to maintain the inhibitory activity the following structural elements are necessary: a hydroxyl group or ketone in $C_1$ and $C_8$, hydroxyl groups in position $C_{21}$ and $C_{23}$, a determined spatial relation among the functional groups and an ansa bridge (cfr. P. Sensi, *P. Appl. Chem.* 1975, vol. 41, pp. 15-29).

Hundreds of semisynthetic rifamycins have been prepared with the hope of obtaining substances with better biological activities; most of them present modifications in the positions $C_4$ (rifamide) and $C_3$ (rifampicin). These structural changes do not affect the action of the substances over the enzyme in a critical way, but modify other important parameters such as the cellularcelular membrane permeability, the pharmacokinetic properties and the resortion (cfr. S. Lancini et al., "Structure-Activity Relationship among the Semisynthetic Antibiotics". D. Perlmann, Ed., Academic Press, N.Y. 1977, pp. 531-600).

The spiropiperidylrifamycins are a class of semisynthetic antibiotics derived from the rifamycins in which the carbons $C_3$ and $C_4$ are incorporated into an imidazol ring, which itself has a spirocyclic piperidine (cfr. A. Sanfilippo et al., *J. Antib.* 1980, vol. 33, p. 1193; L. Marsili et al., *J. Antib.* 1981, vol. 34, p. 1033). The nitrogen atom from the piperidine ring may have different substituents (linear and ramificated alkyl radicals, functionalized alkyl, benzyl, acetyl and ethoxycarbonyl) (cfr. U.S. Pat. No. 4,086,225; DE 2,825,445-A). Among these spiropiperidylrifamycins, the rifabutin has been used with therapeutic purposes as a multidrug for the treatment of tuberculosis and against the *Mycobacterium Avium-Mycobacterium intracellulare* Complex (MAC) infections in patients with HIV (cfr. U.S. Pat. No. 4,219,478).

From what is known in the art, it is very desirable to provide new drugs possessing biological activity, not only against *Mycobacterium tuberculosis*, but also against mycobacterial infections in general.

SUMMARY OF THE INVENTION

Described herein is a new structural derivative of spiropiperidylrifamycins with antimycobacterial activity that is comparable and, in many cases better, than the one shown by the existing drugs at present time.

Described herein is a compound of formula (1), their pharmaceutically acceptable salts and their solvates, including hydrates, wherein: $R^1$ is a radical selected from hydrogen and $(C_1-C_4)$-alkyl; $R^2$ is selected from the group consisting of hydroxy-$(C_1-C_4)$-alkyl, phenyl, phenyl mono-substituted phenyl, and phenyl di-substituted in positions 3 and 4, the phenyl substituents being selected from the group consisting of halogen, $(C_1-C_4)$-alkyl and $(C_1-C_4)$-alcoxyl; $R^3$ is selected from the group consisting of phenyl, phenyl mono-substituted phenyl, and phenyl di-substituted in positions 3 and 4 being the phenyl substituents selected from the group consisting of halogen, $(C_1-C_4)$-alkyl and $(C_1-C_4)$-alcoxyl; and $R^4$ is selected from the group consisting of hydrogen, $(C_1-C_4)$-alkyl, allyl and homoallyl.

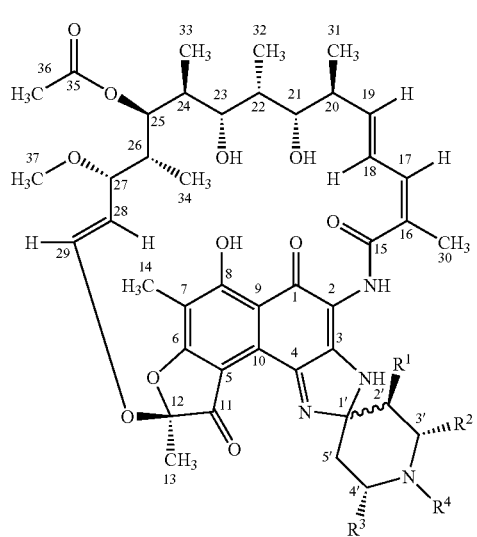

(1)

In a preferred embodiment, the compounds of formula (1) are those wherein, when $R^2$ and $R^3$ are phenyl mono- or di-substituted, the substituents of the phenyl are independently selected from halogen and $(C_1-C_4)$-alkoxyl. In a much preferred embodiment, the substituent is the methoxyl.

The compounds of formula (1) especially preferred herein are shown in Table 1. Said compounds have been denominated in the present specification indistinctly as compounds of formula (1) or as 1 RFA.

TABLE 1

| Comp. 1 | $R^1$ | $R^2$ | $R^3$ | $R^4$ | Tr (h) | Rto. (%) | Rel. Diast. (M:m) crude |
|---|---|---|---|---|---|---|---|
| RFA 1 | Me | CH$_2$OH | Ph | H | 48 | 27 | 90:10 |
| RFA 2 | Me | CH$_2$OH | 4-MeO-Ph | H | 48 | 33 | 9010 |

TABLE 1-continued

| Comp. 1 | $R^1$ | $R^2$ | $R^3$ | $R^4$ | Tr (h) | Rto. (%) | Rel. Diast. (M:m) crude |
|---|---|---|---|---|---|---|---|
| RFA 3 | H | Ph | Ph | H | 5 | 71 | 68:32 |
| RFA 4 | H | 4-MeO-Ph | 4-MeO-Ph | H | 3 | 69 | 74:26 |
| RFA 5 | H | 4-F-Ph | 4-F-Ph | H | 3.5 | 70 | 75:25 |
| RFA 6 | H | 2-I-Ph | 2-I-Ph | H | 6 | 75 | 80:20 |
| RFA 7 | H | Ph | Ph | Allyl | 1.5 | 68 | 73:27 |
| RFA 8 | H | 4-MeO-Ph | 4-MeO-Ph | Allyl | 2 | 65 | 78:22 |
| RFA 9 | H | 3,4-di-MeO-Ph | 3,4-di-MeO-Ph | Allyl | 3 | 62 | 76:24 |
| RFA 10 | H | 4-F-Ph | 4-F-Ph | Allyl | 3 | 69 | 76:24 |
| RFA 11 | H | 4-Cl-Ph | 4-Cl-Ph | Allyl | 4.4 | 67 | 74:26 |
| RFA 12 | H | 2-Br-Ph | 2-Br-Ph | Allyl | 2 | 63 | 75:25 |
| RFA 13 | H | 3-Br-Ph | 3-Br-Ph | Allyl | 3 | 63 | 80:20 |
| RFA 14 | H | 2-I-Ph | 2-I-Ph | Allyl | 5 | 69 | 76:24 |
| RFA 15 | H | Ph | Ph | homo-allyl | 1.5 | 60 | 73:27 |
| RFA 16 | H | Ph | Ph | Bu | 4 | 62 | 75:25 |

In Table, M means majority diastereoisomer and m means minority diastereoisomer.

In Table, M means majority diastereoisomer and m means minority diastereoisomer.

Also described herein is a process for the preparation of the compound of formula (1) defined previously, wherein the process may entail carrying out a condensation reaction between the substituted 4-piperidones of formula (2) and the intermediate 3-amino-4-iminorifamycin S of formula (3). The procedure may take place in soft conditions and with good yield. Schema 1 illustrates one way of accomplishment of said procedure.

Schema 1:

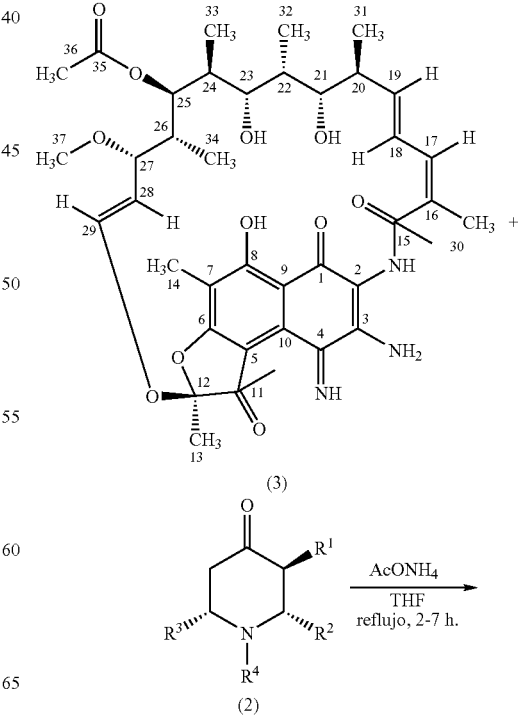

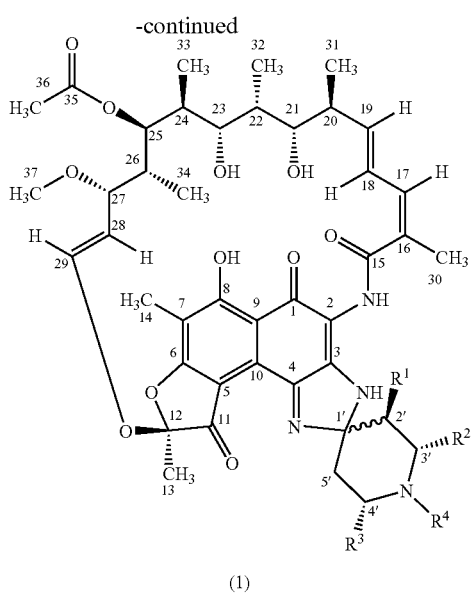

(1)

The intermediate of formula (3) may be obtained from the Rifamycin S (cfr. U.S. Pat. No. 4,017,481 and DE 2,825,445-A). The 4-piperidones of formula (2) may be prepared by known procedures (cfr J. Barluenga et al., *J. Org. Chem.* 1993, vol. 58, pp. 3391; J. Barluenga et al., *J. Org. Chem.* 1998, vol. 63, p. 3918; A-B. García et al., *Tetrah. Letter* 2004, vol. 45, p. 4357]. Said 4-piperidones of formula (2) can be disubstituted or trisubstituted. The preferred compounds of formula (2) are shown 2.

TABLE 2

Preferred 4-piperidones of formula (2):

| Compound 2 | $R^1$ | $R^2$ | $R^3$ | $R^4$ |
|---|---|---|---|---|
| 2a | Me | CH$_2$OH | Ph | H |
| 2b | Me | CH$_2$OH | 4-MeO-Ph | H |
| 2c | H | Ph | Ph | H |
| 2d | H | 4-MeO-Ph | 4-MeO-Ph | H |
| 2e | H | 4-F-Ph | 4-F-Ph | H |
| 2f | H | 2-I-Ph | 2-I-Ph | H |
| 2g | H | Ph | Ph | Allyl |
| 2h | H | 4-MeO-Ph | 4-MeO-Ph | Allyl |
| 2i | H | 3,4-di-MeO-Ph | 3,4-di-MeO-Ph | Allyl |
| 2j | H | 4-F-Ph | 4-F-Ph | Allyl |
| 2k | H | 4-Cl-Ph | 4-Cl-Ph | Allyl |
| 2l | H | 2-Br-Ph | 2-Br-Ph | Allyl |
| 2m | H | 3-Br-Ph | 3-Br-Ph | Allyl |
| 2n | H | 2-I-Ph | 2-I-Ph | Allyl |
| 2o | H | Ph | Ph | homoallyl |
| 2p | H | Ph | Ph | Bu |

Preferably, the procedure may be carried out in a non-halogenated solvent, and in presence of a base. More preferably, the solvent may be an ether, and still more preferable the ether may be tetrahydrofuran (THF). Also preferably, the base used may be ammonium acetate. The reaction may be carried out at a temperature of between about room temperature and about the reflux temperature of the solvent, more preferably, at about the reflux temperature of the solvent. The reaction may be monitored until there is no detection of the intermediate 3-amino-4-iminorifamycin S. Said monitoring may be carried out by HPLC (High Performance Liquid Chromatography) and TLC (Thin Layer Chromatography).

The spiropiperidylrifamycin derivatives obtained may be purified from the crude of reaction and isolated through conventional techniques as crystallization or freeze drying.

The basic nature of the compounds of general formula (1) allows their isolation in the form of their pharmaceutically acceptable salts. The compounds of formula (1) may be converted into their salts and the salts may be converted into the free compounds, through conventional methods.

This procedure of synthesis of spiroperidylrifamycin derivatives of formula (1) gives rise to the formation of a new stereogenic centre in the spiranic carbon atom C-1'. It constitutes the first known reaction, in which enantiomerically pure 4-piperidones are used in the condensation reaction with the intermediate 3-amino-4-iminorifamycin S, as well as of the use of substituted 4-piperidones in the positions 2, 3 or 6 of the ring.

As an example, the reaction of condensation carried out with the enantiomeric trisubstituted 4-piperidones (−)-(2R, 3S,6S)-2-hydroxymethyl-3-methyl-6-phenyl-4-piperidone (2a) and (−)-(2R,3S,6S)-2-hydroxymethyl-3-methyl-6-p-methoxyphenyl-4-piperidone) (2b) may provide the corresponding spiropiperidylrifamycins of formula (1) as a mixture of diastereoisomers (majority (M)/minority (m)) respect to the spiranic carbon C-1'. The proportion of each one is determined by HPLC. In Schema 2 the structure of the diastereoisomers is shown. The mixture of diastereoisomers can be separated and isolated through TLC preparative.

Exhaustive studies 2D of $^1$H and $^{13}$C-NMR, based on the spectra of gHSQC and gHMBC, have been undertaken to assign all the signals of the molecule, as well as the configuration of the new stereogenic centre, the spiranic carbon C-1', observing a higher screening (minor values of ppm) in the hydrogen signal of the NH-3 in the spectrum of $^1$H-NMR of the majority diastereoisomer in relation with the minority (between about 0.6 and about 1.4 ppm). (Cfr. E. Rubio et al., *Magn. Reson. Chem.* 2005, vol. 43, pp. 269-282).

Schema 2. - Structure of the diastereoisomers

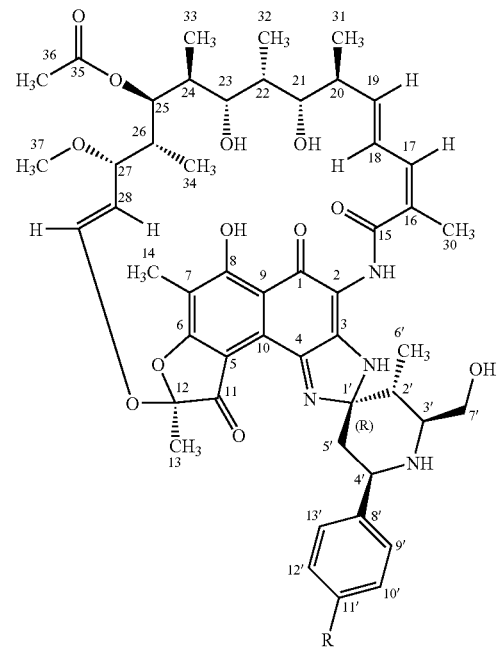

1 RFA 1M (R = H)
1 RFA 2M (R = OCH$_3$)

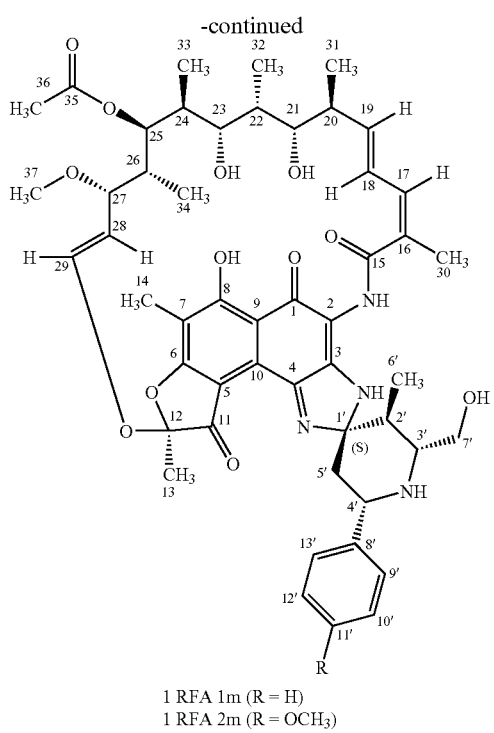

1 RFA 1m (R = H)
1 RFA 2m (R = OCH₃)

Also described herein is a pharmaceutical composition for the treatment of mycobacterial infections, that comprises a therapeutically effective quantity of the compound of formula (1) defined previously, together with suitable quantities of pharmaceutically acceptable excipients or carriers.

The compounds of formula (1) show a strong biological activity. The Examples 33-34 of this specification show the results obtained in the biological activity study. The assayed compounds show in vitro a strong antimycobacterial general activity, even higher than rifampicin-rifabutin in the reference strain *Mycobacterium tuberculosis* ATCC 37837. Several compounds of formula (1) were also assayed against five strains of *Mycobacterium avium-intracellulare* complex, being the five strains sensitive at least to three of the compounds of formula (1) studied. These strains show resistance to rifampicin-rifabutin. With respect to the four strains of *Mycobacterium kansasii* all the compounds of formula (1) studied, had a similar behaviour to rifampicin-rifabutin.

Also described herein is the use of the compound of formula (1) defined previously, for the preparation of a drug for the treatment of a mycobaterial infection, preferably for an infection caused by the following bacteria: *Mycobacterium tuberculosis, Mycobacterium avium-intracellulare* complex or *Mycobacterium kansasii*.

This may include a method of treatment of a mammal, including a human, that suffers a mycobacterial infection, preferably caused by the following bacteria: *Mycobacterium tuberculosis, Mycobacterium avium-intracellulare* complex or *Mycobacterium kansasii*, which may involve the administration to said mammal a therapeutically effective quantity of the compound of formula (1) defined previously, together with suitable quantity of pharmaceutically acceptable excipients or carriers.

Throughout the description and claims the word "comprise" and its variants is not intended to exclude other technical features, additives, components or steps. The abstract of this application is incorporated herein as reference. For those skilled in the art, other objects, advantages and features of the invention will become apparent deduced in part through the description and in part by practice of the invention. The following examples are provided by way of illustration, and are not intended to be limiting of the present invention.

EXAMPLES

The nuclear magnetic resonance spectra and the studies of bidimensional correlation were carried out in a Bruker AV-400 operating in a frequency of 400.13 y 100.61 MHz for $^1$H and $^{13}$C respectively, using a reverse probe QXI $^1$H/$^{13}$C/$^{15}$N/$^{31}$P de 5 mm including a bovine of gradient in the axis Z. The samples prepared contained about 30 to about 50 mg of compound. Deutered benzene ($C_6D_6$) was used, except in the case of the compound 1 RFA-1m in which deutered chlorophorm ($CDCl_3$) was used as solvent. The chemical displacements are expressed in ppm (parts per million) and are referred to a residual signal of the solvent ($\delta$ 7.16 for $^1$H and of 128.39 for $^{13}$C).

The high resolution mass spectra were carried out in a Finnigan-Matt 95, using electronic impact procedures, electro spray positive (ES pos.) and FAB+. The fusion points have not been corrected and were measured in a Büchi-Tottoli apparatus. The thin layer chromatography (TLC) was done over silica gel plates (Merck 60 G). For the column cromatography silica gel 60 (230-240 mesh) as stationary phase was used. The preparative cromatography was carried out using glass plates (20×20 cm) of silica gel (Merck 60 $F_{254}$).

In the case of the products 1 RFA-1 and 1 RFA-2, the crudes from the reactions were purified by HPLC using a Waters LC Module I plus apparatus, at room temperature, using a detector V-UV Photodiode-Array and a reverse phase column (Kromasil 100 C8 5 μm 25×1.0). The mobile phase used was a mixture of about 1:1 of acetonitrile:phosphate buffers, $(NH_4)H_2PO_4$ (0.05 M) at pH 6.8 and flow of 5.5 ml/min.

General Method for the Preparation of the Compounds of Formula (1): 1 RFA-1 and 1 RFA-2:

About 100 mg of piperidone (2a-b) may be dissolved in about 15 ml of tetrahydrofuran (THF) at room temperature, next about 2 equivalents of ammonium acetate and about one equivalent of the intermediate 3-amino-4-iminorifamycin S (3) are added. The reaction mixture is stirred at reflux for about 24 hours. After this time, the reaction mixture may be allowed to reach room temperature and an addition is made of about 0.5 equivalents more of the intermediate 3-amino-4-iminorifamycin S (3) and the mixture may be stirred at reflux for about 24 hours more. After this time the mixture may be allowed to reach about room temperature and diethyl ether (about 30 ml) is added, it may be filtered over celita and it may be washed again with diethyl ether (about 2×15 ml). The organic phase may be washed with a buffer solution (about pH 7.6), of $(NH_4)H_2PO_4$ 0.05 M (about 3×15 ml), it may be dried with sodium sulphate anhydrous and concentrated to dryness. The solid obtained may be a mixture comprised mainly of the excess of the intermediate 3-amino-4-iminorifamycin S (3) and the new compounds of formula (1), which may be washed with acetic acid at about 4% (as many times as necessary so that TLC does not appear violet) and passed to the aqueous phase in acetate form while the precursor may be kept in the etheria phase. The violet aqueous phase may be extracted with chloroform, leaving long decantation periods. The organic layer therefore obtained, may be washed with the buffer solution mentioned previously (portions of about 30 ml) until the waters of washing have about a neutral pH. The organic phase may be dried with sodium sulphate anhydrous and filtered. The solvents may be evaporated at reduced pressure and may result in a residue that corresponds mainly to the mixture of diastereisomers (90:10), which may be separated by HPLC using as eluent a mixture phosphates buffer:acetonitrile 1:1 at pH 6.8. The products may be isolated by chloroform extraction ($CHCl_3$), dryed over sodium sulphate anhydrous, filtered and evaporation of the selected chromatographic fractions. The products are presented as violet solids. The product is isolated by freeze drying, extraction and evaporation or crystallization of the selected chromatographic fractions Following this general method the compounds of the Examples 1 to 4 were prepared.

Example 1

Preparation of 4-deoxo-3,4-[(2R)-2-spiro(6-phenyl-2-hydroxymethyl-3-methyl-4-piperidil)-2,5-dihydro-1H-imidazo]rifamycin S (1 RFA-1M)

Following the general procedure of RFA (1-2) from the compound 2a shown in Table 2 and the compound (3) shown in Schema 1, the compound of the title was obtained that presents approximately the following data: HRMS (ESI pos): 911.4425 [calculated for (M+1)+: 911.4437]. Elemental anal.: calculated (%) for $C_{50}H_{62}N_4O_{12}$: C, 65.92; H, 6.86; N, 6.15; found: C, 65.81; H, 6.92; N, 6.19. HPLC: t=12, 1 min (Ø=1 ml/min; phosphates buffer:acetonitrile 1:1 a pH=6.8). TLC:Rf: 0.20 (toluene:methanol: ethyl acetate 6:1:1). $^1$H-RMN: 9.10 (NH-2); 8.85 (NH-3).

Example 2

Preparation of 4-deoxo-3,4-[(2S)-2-spiro(6-phenyl-2-hydroxymethyl-3-methyl-4-piperidil)-2,5-dihydro-1H-imidazo]rifamycin S (1 RFA-1m)

Following the general procedure of RFA (1-2) from the compound 2a shown in Table 2 and the compound (3) shown in Schema 1, the compound of the title was obtained that presents approximately the following data: P.f.: 159-62° C. (desc.). HRMS (EI): 910.4388 (calculated for M+: 910, 4364). Elemental anal.: calculated (%) for $C_{50}H_{62}N_4O_{12}$: C 65.92; H, 6.86; N, 6.15; finding: C, 65.99; H, 6.71; N, 6.00. HPLC: t=8.6 min (Ø=1 ml/min; phosphates buffer: acetonitrile 1:1 a pH=6.8). TLC: Rf: 0.39 (toluene:methanol:ethyl acetate 6:1:1). $^1$H-RMN: 8.98 (NH-2); 8.18 (NH-3).

Example 3

Preparation of 4-deoxo-3,4-[(2R)-2-spiro(2-hydroxymethyl-3-methyl-6-p-methoxyphenyl-4-piperidil)-2,5-dihydro-1H-imidazo]rifamycin S (1 RFA-2M)

Following the general procedure of 1RFA (1-2) from the compound 2b shown in Table 2 and the compound (3) shown in Schema 1, the compound of the title was obtained that presents approximately the following data: P.f.: 171-74° C. (desc.). HRMS (ESI pos): 941.4546 [calculated for (M+1)+: 941.4543]. Elemental anal.: calculated (%) for $C_{51}H_{64}N_4O_{13}$: C, 65.09; H, 6.85; N, 5.95; found: C, 65.22; H, 6.79; N, 5.82. HPLC: t=11.9 min (Ø=1 ml/min; phosphates buffer:acetonitrile 1:1 a pH=6.8). TLC: Rf: 0.33 (toluene:methanol:ethyl acetate 6:1:1). $^1$H-RMN: 8.99 (NH-2); 8.72 (NH-3).

Example 4

Preparation of 4-deoxo-3,4-[(2S)-2-spiro(2-hydroxymethyl-3-methyl-6-p-methoxyphenyl-4-piperidil)-2,5-dihydro-1H-imidazo]rifamycin S (1 RFA-2m)

Following the general procedure of 1RFA (1-2) from the compound 2b shown in Table 2 and the compound (3) shown in Schema 1, the compound of the title was obtained that presents approximately the following data: P.f.: 168-72° C. (desc.). HRMS (FAB+): 941.4543 (calculated for [M+1]+: 941.4548). Elemental anal.: calculated (%) for $C_{51}H_{64}N_4O_{13}$: C, 65.09; H, 6.85; N, 5.95; found: C, 65.30; H, 6.74; N, 5.78. HPLC: t=9.1 min (Ø=1 ml/min; phosphates buffer:acetonitrile 1:1 a pH=6.8). TLC:Rf: 0.35 (toluene:methanol:ethyl acetate 6:1:1). $^1$H-RMN: 8.76 (NH-2); 9.47 (NH-3).

General Method for the Derivatives 1RFA (3-16) Preparation:

About 100 mg of 4-piperidone (2c-p) is dissolved in about 15 ml of THF. About 1 equivalent of the intermediate 3-amino-4-iminorifamycin S (3)) may be added, followed by 2 equivalents of ammonium acetate. The reaction may be heated to reflux and monitored by TLC and HPLC until no detection of the starting materials (about 1-6 hours). The mixture is allowed to reach about room temperature and about 30 ml of ether are added, leaving the dissolution to stir for about 15 minutes. The mixture of reaction may be extracted, by washing the organic layer three times with a buffer solution of $(NH_4)H_2PO_4$ (pH 7.6). The organic layer may be dried with $Na_2SO_4$ anhydrous, filtered, and the solvents are removed at reduced pressure obtaining a solid of pink-violet colour formed mainly by a mixture of the two diastereoisomers looked for, whose proportion is obtained by HPLC (mixtures of acetonitrile-water) in reverse phase. The purification of the two diastereoisomers may be carried out by preparative TLC using as eluents mixtures of: toluene:ethyl acetate:methanol/in a ratio of about 6:1:1. The two diastereisomers (violet compounds) separated in the plate may be released from the support of glass with the help of a spatula and dissolved in chloroform. The silica gel may be filtered and the solvents removed at reduced pressure, obtaining the two diastereoisomers (M/m) as violet solids. In the case that the diastereoisomers do not separate well, it may be necessary to do a second purification by preparative TLC using eluent mixtures of hexane: THF:triethylamine/in a ratio of about 5:4:1. The product may be isolated by freeze drying, extraction and evaporation or crystallization of the selected chromatographic fractions.

Following this general method the compounds described in the Examples 5 to 32 were prepared.

Example 5

Preparation of 4-deoxo-3,4-[(2R)-2-spiro(2,6-diphenyl-4-piperidyl)-2,5-dihydro-1H-imidazo]rifamycin S (1 RFA-3M)

Following the general procedure of 1RFA (1-2) from the compound 2c shown in Table 2 and the compound (3) shown in Schema 1, the compound of the title was obtained that presents approximately the following data: P.f.: 164-66° C. (desc.). HRMS (ESI pos): 943.4469 [calculated for (M+1)+: 943.4488]. Elemental anal.: calculated (%) for $C_{54}H_{62}N_4O_{11}$: C, 68.77; H, 6.63; N, 5.94; found: C, 68.47; H, 6.59; N, 6.22. HPLC: t=11.2 min, (Ø=1 ml/min; Acetonitrile:water/65:35). TLC: Rf: 0.52 (toluene:methanol:ethyl acetate 6:1:1); 0.33 (hexane:THF:triethylamine 5:4:1) $^1$H-RMN: 8.53 (NH-2); 8.99 (NH-3).

Example 6

Preparation of 4-deoxo-3,4-[(2S)-2-spiro(2,6-diphenyl-4-piperidyl)-2,5-dihydro-1H-imidazo]rifamycin S (1 RFA-3m)

Following the general procedure of 1RFA (3-16) from the compound 2c shown in Table 2 and the compound (3) shown in Schema 1, the compound of the title was obtained that presents approximately the following data: P.f.: 168-70° C. (desc.). HRMS (ESI pos): 943.4469 [calculated for (M+1)+: 943.4488]. Elemental anal.: calculated (%) for $C_{54}H_{62}N_4O_{11}$: C, 68.77; H, 6.63; N, 5.94; found: C, 68.63; H, 6.69; N, 5.99. HPLC: t=9.6 min, (Ø=1 ml/min; Acetonitrile:water/65:35). TLC: Rf: 0.56 (toluene:methanol:ethyl acetate 6:1:1); 0.23 (hexane:THF:triethylamine 5:4:1). $^1$H-RMN: 8.73 (NH-2); 9.98 (NH-3).

Example 7

Preparation of 4-deoxo-3,4-[(2R)-2-spiro[2,6-bis(4-methoxiphenyl)-4-piperidyl]-2,5-dihydro-1H-imidazo]rifamycin S (1 RFA-4M)

Following the general procedure of 1RFA (3-16) from the compound 2d shown in Table 2 and the compound (3) shown in Schema 1, the compound of the title was obtained that presents approximately the following data: P.f.: 166-68° C. (desc.). HRMS (ESI pos): 1003.4706 [calculated for (M+1)+: 1003.4699]. Elemental anal.: calculated (%) for $C_{56}H_{66}N_4O_{13}$: C, 67.05; H, 6.63; N, 5.59; found: C, 66.87; H, 6.43; N, 5.48. HPLC: t=8.2 min; (Ø=1 ml/min; Acetonitrile:water/65:35). TLC: Rf: 0.49 (toluene:methanol:ethyl acetate 6:1:1); 0.25 (hexane:THF:triethylamine 5:4:1). $^1$H-RMN: 8.56 (NH-2); 9.05 (NH-3).

Example 8

Preparation of 4-deoxo-3,4-[(2S)-2-spiro[2,6-bis(4-methoxyphenyl)-4-piperidil]-2,5-dihydro-1H-imidazo]rifamycin S (1 RFA-4m)

Following the general procedure of 1RFA (3-16) from the compound 2d shown in Table 2 and the compound (3) shown in Schema 1, the compound of the title was obtained that presents approximately the following data: P.f.: 173-75° C. (desc.). HRMS (ESI pos): 1003.4691 [calculated for (M+1)+: 1003.4699]. Elemental anal.: calculated (%) for $C_{56}H_{66}N_4O_{13}$: C, 67.05; H, 6.63; N, 5.59; found: C, 66.92; H, 6.71; N, 5.20. HPLC: t=7.2 min; (Ø=1 ml/min; Acetonitrile:water/65:35). TLC: Rf: 0.54 (toluene:methanol:ethyl acetate 6:1:1); 0.18 (hexane:THF:triethylamine 5:4:1). $^1$H-RMN: 8.65 (NH-2); 10.12 (NH-3).

Example 9

Preparation of 4-deoxo-3,4-[(2R)-2-spiro[2,6-bis(4-fluorophenyl)-4-piperidil]-2,5-dihydro-1H-imidazo]rifamycin S (1 RFA-5M)

Following the general procedure of 1RFA (3-16) from the compound 2e shown in Table 2 and the compound (3) shown in Schema 1, the compound of the title was obtained that presents approximately the following data: P.f.: 172-75° C. (desc.). HRMS (ESI pos): 979.4292 [calculated for (M+1)+: 979.4299]. Elemental anal.: calculated (%) for $C_{54}H_{60}F_2N_4O_{11}$: C, 66.24; H, 6.18; N, 5.72; found: C, 66.15; H, 6.16; N, 5.47. HPLC: t=10 min; (Ø=1 ml/min; Acetonitrile:water/65:35). TLC:Rf: 0.55 (toluene:methanol:ethyl acetate 6:1:1); 0.30 (hexane:THF:triethylamine 5:4:1). $^1$H-RMN: 8.70 (NH-2); 8.96 (NH-3).

Example 10

Preparation of 4-deoxo-3,4-[(2S)-2-spiro[2,6-bis(4-fluorophenyl)-4-piperidil]-2,5-dihydro-1H-imidazo]rifamycin S (1 RFA-5m)

Following the general procedure of 1RFA (3-16) from the compound 2e shown in Table 2 and the compound (3) shown in Schema 1, the compound of the title was obtained that presents approximately the following data: P.f.: 145° C. (desc.). HRMS (ESI pos): 979.4274 [calculated for (M+1)+: 979.4299]. Elemental anal.: calculated (%) for $C_{54}H_{60}F_2N_4O_{11}$: C, 66.24; H, 6.18; N, 5.72; found: C, 66.43; H, 6.53; N, 5.33. HPLC: t=10.9 min; (Ø=1 ml/min; Acetonitrile:water/65:35). TLC: Rf: 0.59 (toluene:methanol:ethyl acetate 6:1:1); 0.19 (hexane:THF:triethylamine 5:4:1). $^1$H-RMN: 8.83 (NH-2); 9.94 (NH-3).

Example 11

Preparation of 4-deoxo-3,4-[(2R)-2-spiro[2,6-bis(2-iodophenyl)-4-piperidil]-2,5-dihydro-1H-imidazo]rifamycin S (1 RFA-6M)

Following the general procedure of 1RFA (3-16) from the compound 2f shown in Table 2 and the compound (3) shown in Schema 1, the compound of the title was obtained that presents approximately the following data: P.f.: 137-39° C. (desc.). HRMS (ESI pos): 1195.2430 [calculated for (M+1)+: 1195.2421]. Elemental anal.: calculated (%) for $C_{54}H_{60}I_2N_4O_{11}$: C, 54.28; H, 5.06; N, 4.69; found: C, 54.01; H, 5.12; N, 4.76. HPLC: t=20.1 min; (Ø=1 ml/min; Acetonitrile:water/65:35). TLC: Rf: 0.55 (toluene:methanol:ethyl acetate 6:1:1); 0.30 (hexane:THF:triethylamina 5:4:1). $^1$H-RMN: 9.01 (NH-2); 8.63 (NH-3).

Example 12

Preparation of 4-deoxo-3,4-[(2S)-2-spiro[2,6-bis(2-iodophenyl)-4-piperidil]-2,5-dihydro-1H-imidazo]-rifamycin S (1 RFA-6m)

Following the general procedure of 1RFA (3-16) from the compound 2f shown in Table 2 and the compound (3) shown in Schema 1, the compound of the title was obtained that presents approximately the following data: HPLC: t=28.7 min; (Ø=1 ml/min; cetonitrile:water/65:35).

Example 13

Preparation of 4-deoxo-3,4-[(2R)-2-spiro(N-allyl-2,6-diphenyl-4-piperidil)-2,5-dihydro-1H-imidazo]rifamycin S (1 RFA-7M)

Following the general procedure of 1RFA (3-16) from the compound 2g shown in Table 2 and the compound (3) shown in Schema 1, the compound of the title was obtained that presents approximately the following data:P.f.: 175-77° C. (desc.). HRMS (ESI pos): 983.4778 [calculated for (M+1)+: 983.4801]. Elemental anal.: calculated (%) for $C_{57}H_{66}N_4O_{11}$: C, 69.63; H, 6.77; N, 5.70; found: C, 69.54; H, 6.89; N, 5.93. HPLC: t=42.7 min; (Ø=1 ml/min; acetonitrile:water/65:35). TLC:Rf: 0.55 (toluene:methanol:ethyl acetate 6:1:1); 0.32 (hexane:THF:triethylamine 5:4:1). $^1$H-RMN: 8.62 (N-2); 8.89 (NH-3).

Example 14

Preparation of 4-deoxo-3,4-[(2S)-2-spiro(N-allyl-2,6-diphenyl-4-piperidil)-2,5-dihydro-1H-imidazo]-rifamycin S (1 RFA-7m)

Following the general procedure of 1RFA (3-16) from the compound 2g shown in Table 2 and the compound (3) shown in Schema 1, the compound of the title was obtained that presents approximately the following data: P.f.: 169-72° C. (desc.). HRMS (ESI pos): 983.4782 [calculated for (M+1)+: 983.4801]. Elemental anal.: calculated (%) for $C_{57}H_{66}N_4O_{11}$: C, 69.63; H, 6.77; N, 5.70; found: C, 69.32; H, 7.09; N, 6.08.). HPLC: t=45 min; (Ø=1 ml/min; acetonitrile:water/65:35). TLC: Rf: 0.54 (toluene:methanol:ethyl acetate 6:1:1); 0.21 (hexane:THF:triethylamine 5:4:1). $^1$H-RMN: 8.61 (NH-2); 10.28 (NH-3).

Example 15

Preparation of 4-deoxo-3,4-[(2R)-2-spiro(N-allyl-2,6-bis(4-methoxyphenyl)-4-piperidil)-2,5-dihydro-1H-imidazo]rifamycin S (1 RFA-8M)

Following the general procedure of 1RFA (3-16) from the compound 2h shown in Table 2 and the compound (3) shown in Schema 1, the compound of the title was obtained that presents approximately the following data: P.f.: 158-61° C. (desc.). HRMS (ESI pos): 1043.5012 [calculated for (M+1)+: 1043.5012]. Elemental anal.: calculated (%) for $C_{59}H_{70}N_4O_{13}$: C, 67.93; H, 6.76; N, 5.37; found: C, 67.75; H, 6.58; N, 5.34.). HPLC: t=9.3 min; (Ø=1 ml/min; acetonitrile:water/85:15). TLC: Rf: 0.46 (toluene:methanol:ethyl acetate 6:1:1); 0.29 (hexane:THF:triethylamine 5:4:1). $^1$H-RMN: 8.65 (NH-2).

Example 16

Preparation of 4-deoxo-3,4-[(2S)-2-spiro(N-allyl-2,6-bis(4-methoxyphenyl)-4-piperidil)-2,5-dihydro-1H-imidazo]rifamycin S (1 RFA-8m)

Following the general procedure of 1RFA (3-16) from the compound 2h shown in Table 2 and the compound (3) shown in Schema 1, the compound of the title was obtained that presents approximately the following data: P.f.: 157-59° C. (desc.). HRMS (ESI pos): 1043.5016 (calculated for [M+1)+: 1043.5012]. Elemental anal.: calculated (%) for $C_{59}H_{70}N_4O_{13}$: C, 67.93; H, 6.76; N, 5.37; found: C, 68.13; H, 6.83; N, 5.12. HPLC t=8.0 min; (Ø=1 ml/min; acetonitrile:water/85:15). TLC: Rf: 0.49 (toluene:methanol:ethyl acetate 6:1:1); 0.18 (hexane:THF:triethylamine 5:4:1). $^1$H-RMN: 8.74 (NH-2); 10.22 (NH-3).

Example 17

Preparation of 4-deoxo-3,4-[(2R)-2-spiro(N-allyl-2,6-bis(3,4-dimethoxyphenyl)-4-piperidil)-2,5-dihydro-1H-imidazo]rifamycin S (1 RFA-9M)

Following the general procedure of 1RFA (3-16) from the compound 2l shown in Table 2 and the compound (3) shown in Schema 1, the compound of the title was obtained that presents approximately the following data: HRMS (ESI pos): 1103.5229 [calculated for (M+1)+: 1103.5223]. Elemental anal.: calculated (%) for $C_{61}H_{74}N_4O_{15}$: C, 66.41; H, 6.76; N, 5.08; found: C, 66.18; H, 6.80; N, 5.17. HPLC: t=4.9 min; (Ø=1 ml/min; acetonitrile:water/85:15). TLC: Rf: 0.38 (toluene:methanol:ethyl acetate 6:1:1); 0.15 (hexane:THF:triethylamine 5:4:1). $^1$H-RMN: 8.45 (NH-2); 8.95 (NH-3).

Example 18

Preparation of 4-deoxo-3,4-[(2S)-2-spiro(N-allyl-2,6-bis(3,4-dimethoxyphenyl)-4-piperidil)-2,5-dihydro-1H-imidazo]rifamycin S (1 RFA-9m)

Following the general procedure of 1RFA (3-16) from the compound 2l shown in Table 2 and the compound (3) shown in Schema 1, the compound of the title was obtained that presents approximately the following data: HRMS (ESI pos): 1103.5229 [calculated for (M+1)+: 1103.5223]. Elemental anal.: calculated (%) for $C_{61}H_{74}N_4O_{15}$: C, 66.41; H, 6.76; N, 5.08; found: C, 66.25; H, 6.91; N, 5.10. HPLC: t=3.2 min; (Ø=1 ml/min; acetonitrile:water/85:15). TLC: Rf: 0.43 (toluene:methanol:ethyl acetate 6:1:1); 0.08 (hexane:THF:triethylamine 5:4:1). $^1$H-RMN: 8.59 (NH-2); 10.46 (NH-3).

Example 19

Preparation of 4-deoxo-3,4-[(2R)-2-spiro(N-allyl-2,6-bis(4-fluorophenyl)-4-piperidil)-2,5-dihydro-1H-imidazo]rifamycin S (1 RFA-10M)

Following the general procedure of 1RFA (3-16) from the compound 2j shown in Table 2 and the compound (3) shown in Schema 1, the compound of the title was obtained that presents approximately the following data: P.f.: 139-41° C. (desc.). HRMS (ESI pos): 1019.4606 [calculated for (M+1)+: 1019.4612]. Elemental anal.: calculated (%) for $C_{57}H_{64}F_2N_4O_{11}$: C, 67.18; H, 6.33; N, 5.50; found: C, 67.00; H, 6.44; N, 5.71). HPLC: t=5.7 min; (Ø=1 ml/min; acetonitrile:water/85:15). TLC: Rf: 0.52 (toluene:methanol:ethyl acetate 6:1:1); 0.30 (hexane:THF:triethylamine 5:4:1). $^1$H-RMN: 8.71 (NH-2); 8.82 (NH-3).

Example 20

Preparation of 4-deoxo-3,4-[(2S)-2-spiro(N-allyl-2,6-bis(4-fluorophenyl)-4-piperidil)-2,5-dihydro-1H-imidazo]rifamycin S (1 RFA-10m)

Following the general procedure of 1RFA (3-16) from the compound 2j shown in Table 2 and the compound (3) shown in Schema 1, the compound of the title was obtained that presents approximately the following data: P.f.: 132-35° C. (desc.). HRMS (ESI pos): 1019.4591 [calculated for (M+1)+ 10.15 (NH-3). HPLC: t=4.9 min; (Ø=1 ml/min; acetonitrile:water/85:15). TLC: Rf: 0.52 (toluene:methanol:ethyl acetate 6:1:1); 0.15 (hexane:THF:triethylamine 5:4:1).

Example 21

Preparation of 4-deoxo-3,4-[(2R)-2-spiro(N-allyl-2,6-bis(4-chlorophenyl)-4-piperidil)-2,5-dihydro-1H-imidazo]rifamycine S (1 RFA-11M)

Following the general procedure of 1RFA (3-16) from the compound 2k shown in Table 2 and the compound (3) shown in Schema 1, the compound of the title was obtained that presents approximately the following data: P.f.: 165-68° C. (desc.). HRMS (ESI pos): 1051.4037 [calculated for (M+1)+: 1051.4021]. Elemental anal.: calculated (%) for $C_{57}H_{64}Cl_2N_4O_{11}$: C, 65.07; H, 6.13; N, 5.33; found: C, 65.37; H, 6.04; N, 5.28. HPLC: t=8.6 min, (Ø=1; acetonitrile:water/85:15). TLC: Rf: 0.52 (toluene:methanol:ethyl acetate 6:1:1); 0.33 (hexane:THF:triethylamine 5:4:1). $^1$H-RMN: 8.55 (NH-2); 8.84 (NH-3).

Example 22

Preparation of 4-deoxo-3,4-[(2S)-2-spiro(N-allyl-2,6-bis(4-chlorophenyl)-4-piperidil)-2,5-dihydro-1H-imidazo]rifamycin S (1 RFA-11m)

Following the general procedure of 1RFA (3-16) from the compound 2k shown in Table 2 and the compound (3) shown in Schema 1, the compound of the title was obtained that presents approximately the following data: P.f.: 170-72° C. (desc.). HRMS (ESI pos): 1051.4021 [calculated for (M+1)+: 1051.4021]. Elemental anal.: calculated (%) for $C_{57}H_{64}Cl_2N_4O_{11}$: C, 65.07; H, 6.13; N, 5.33; found: C, 65.24; H, 6.14; N, 5.47. HPLC: t=7.4 min; (Ø=1 ml/min; acetonitrile:water/85:15). TLC:Rf: 0.54 (toluene:methanol:ethyl acetate 6:1:1); 0.13 (hexane:THF:triethylamine 5:4:1). $^1$H-RMN: 8.67 (NH-2); 10.21 (NH-3).

Example 23

Preparation of 4-deoxo-3,4-[(2R)-2-spiro(N-allyl-2,6-bis(2-bromophenyl)-4-piperidil)-2,5-dihydro-1H-imidazo]rifamycin S (1 RFA-12M)

Following the general procedure of 1RFA (3-16) from the compound 2l shown in Table 2 and the compound (3) shown in Schema 1, the compound of the title was obtained that presents approximately the following data: P.f.: 187-89° C. (desc.). HRMS (ESI pos): 1139.3022 (calculated for (M+1)+: 1139.3011). Elemental anal.: calculated (%) for $C_{57}H_{64}Br_2N_4O_{11}$: C, 60.00; H, 5.65; N, 4.91; found: C, 60.34; H, 5.33; N, 4.80. HPLC t=7.8 min; (Ø=1 ml/min; acetonitrile:water/85:15). TLC: Rf: 0.52 (toluene:methanol:ethyl acetate 6:1:1); 0.26 (hexane:THF:triethylamine 5:4:1). $^1$H-RMN: 8.74 (NH-2); 9.99 (NH-3).

Example 24

Preparation of 4-deoxo-3,4-[(2S)-2-spiro(N-allyl-2,6-bis(2-bromophenyl)-4-piperidil)-2,5-dihydro-1H-imidazo]rifamycin S (1 RFA-12m)

Following the general procedure of 1 RFA (3-16) from the compound 2l shown in Table 2 and the compound (3) shown in Schema 1, the compound of the title was obtained that presents approximately the following data: P.f.: 182-85° C. (desc.). HRMS (ESI pos): 1139.2980 [calculated for (M+1)+: 1139.3011]. Elemental anal.: calculated (%) for $C_{57}H_{64}Br_2N_4O_{11}$: C, 60.00; H, 5.65; N, 4.91; found: C, 60.24; H, 5.65; N, 4.79. HPLC: t=8.9 min; (Ø=1 ml/min; acetonitrile:water/85:15). TLC: Rf: 0.60 (toluene:methanol:ethyl acetate 6:1:1); 0.29 (hexane:THF:triethylamine 5:4:1). $^1$H-RMN: 8.73 (NH-2); 10.08 (NH-3).

Example 25

Preparation of 4-deoxo-3,4-[(2R)-2-spiro(N-allyl-2,6-bis(3-bromophenyl)-4-piperidil)-2,5-dihydro-1H-imidazo]-rifamycin S (1 RFA-13M)

Following the general procedure of 1RFA (3-16) from the compound 2m shown in Table 2 and the compound (3) shown in Schema 1, the compound of the title was obtained that presents approximately the following data:P.f.: 132-35° C. (desc.). HRMS (ESI pos): 1139.3015 [calculated for (M+1)+: 1139.3011]. Elemental anal.: calculated (%) for $C_{57}H_{64}Br_2N_4O_{11}$: C, 60.00; H, 5.65; N, 4.91; found: C, 60.15; H, 5.58; N, 4.93. HPLC: t=11.7 min; (Ø=1 ml/min; acetonitrile:water/85:15). TLC: Rf: 0.56 (toluene:methanol:ethyl acetate 6:1:1); 0.32 (hexane:THF:triethylamine 5:4:1). $^1$H-RMN: 8.57 (NH-2); 8.74 (NH-3).

Example 26

Preparation of 4-deoxo-3,4-[(2S)-2-spiro(N-allyl-2, 6-bis(3-bromophenyl)-4-piperidil)-2,5-dihydro-1H-imidazo]-rifamicyn S (1 RFA-13m)

Following the general procedure of 1RFA (3-16) from the compound 2m shown in Table 2 and of the compound (3) shown in Schema 1, the compound of the title was obtained that presents approximately the following data: P.f.: 140-42° C. (desc.). HRMS (ESI pos): 1139.3012 [calculated for (M+1)+: 1139.3011]. Elemental anal.: calculated (%) for $C_{57}H_{64}Br_2N_4O_{11}$: C, 60.00; H, 5.65; N, 4.91; found: C, 60.05; H, 5.79; N, 4.68. $^1$H-RMN: 8.59 (NH-2); 9.01 (NH-3). HPLC t=9.7 min, (Ø=1 ml/min; acetonitrile:water/85:15). TLC: Rf: 0.57 (toluene:methanol:ethyl acetate 6:1:1); 0.11 (hexane:THF:triethylamine 5:4:1). $^1$H-RMN: 8.74 (NH-2); 9.99 (NH-3).

Example 27

Preparation of 4-deoxo-3,4-[(2R)-2-spiro(N-allyl-2, 6-bis(2-iodophenyl)-4-piperidil)-2,5-dihydro-1H-imidazo]-rifamycin S (1 RFA-14M)

Following the general procedure of 1RFA (3-16) from the compound 2n shown in Table 2 and the compound (3) shown in Schema 1, the compound of the title was obtained that presents approximately the following data: P.f.: 163-64° C. (desc.). HRMS (ESI pos): 1235.2716 [calculated for (M+1)+: 1235.2734]. Elemental anal.: calculated (%) for C57H64I2N4O11: C, 55.44; H, 5.22; N, 4.54; found: C, 55.05; H, 5.19; N, 4.15. HPLC: t=10.0 min; (Ø=1 ml/min; acetonitrile:water/85:15). TLC: Rf: 0.53 (toluene:methanol: ethyl acetate 6:1:1); 0.28 (hexane:THF:triethylamine 5:4:1). $^1$H-RMN: 8.74 (NH-2); 8.91 (NH-3).

Example 28

Preparation of 4-deoxo-3,4-[(2S)-2-spiro(N-allyl-2, 6-bis(2-iodophenyl)-4-piperidil)-2,5-dihydro-1H-imidazo]rifamycin S (1 RFA-14m)

Following the general procedure of 1RFA (3-16) from the compound 2n shown in Table 2 and the compound (3) shown in Schema 1, the compound of the title was obtained that presents approximately the following data: P.f.: 149-51° C. (desc.). UV (λ=254 nm): 214.5; 280; 320. HRMS (ESI pos): 1235.2701 [calculated for (M+1)+: 1235.2734]. Elemental anal.: calculated (%) for C57H64I2N4O11: C, 55.44; H, 5.22; N, 4.54; found: C, 55.06; H, 5.03; N, 4.16. HPLC t=13.0 min; (Ø=1 ml/min; acetonitrile:water/65:35). TLC: Rf: 0.60 (toluene:methanol:ethyl acetate 6:1:1); 0.32 (hexane:THF:triethylamine 5:4:1). $^1$H-RMN: 8.82 (NH-2); 10.34 (NH-3).

Example 29

Preparation of 4-deoxo-3,4-[(2R)-2-spiro(N-homoallyl-2,6-diphenyl-4-piperidil)-2,5-dihydro-1H-imidazo]rifamycin S (1 RFA-15M)

Following the general procedure of 1RFA (3-16) from the compound 2o shown in Table 2 and the compound (3) shown in Schema 1, the compound of the title was obtained that presents approximately the following data: HRMS (ESI pos): 997.4953 [calculated for (M+1)+: 997.4957]. Elemental anal.: calculated (%) for $C_{58}H_{68}N_4O_{11}$: C, 69.86; H, 6.87; N, 5.62; found: C, 69.73; H, 6.92; N, 5.71. HPLC t=29.3 min, (Ø=1 ml/min; acetonitrile:water/65:35). TLC: Rf: 0.56 (toluene:methanol:ethyl acetate 6:1:1); 0.36 (hexane:THF:triethylamine 5:4:1). $^1$H-RMN: 8.66 (NH-2); 8.83 (NH-3).

Example 30

Preparation of 4-deoxo-3,4-[(2S)-2-spiro(N-homoallyl-2,6-diphenyl-4-piperidil)-2,5-dihydro-1H-imidazo]rifamycin S (1 RFA-15m)

Following the general procedure of 1RFA (3-16) from the compound 2o shown in Table 2 and the compound (3) shown in Schema 1, the compound of the title was obtained that presents approximately the following data: HRMS (ESI pos): 997.4951 [calculated for (M+1)+: 997.4957]. Elemental anal.: calculated (%) for $C_{58}H_{68}N_4O_{11}$: C, 69.86; H, 6.87; N, 5.62; found: C, 69.99; H, 6.89; N, 5.43. HPLC t=27.0 min; (Ø=1 ml/min; acetonitrile:water/65:35). TLC: Rf: 0.59 (toluene:methanol:ethyl acetate 6:1:1); 0.20 (hexane:THF:triethylamine 5:4:1). $^1$H-RMN: 8.70 (NH-2) 10.26 (NH-3).

Example 31

Preparation of 4-deoxo-3,4-[(2R)-2-spiro(N-butyl-2,6-diphenyl-4-piperidil)-2,5-dihydro-1H-imidazo]rifamycin S (1 RFA-16M)

Following the general procedure of 1RFA (3-16) from the compound 2p shown in Table 2 and the compound (3) shown in Schema 1, the compound of the title was obtained that presents approximately the following data: P.f.: 160-63° C. (desc.). UV (λ=254 nm): 240, 278, 320. HRMS (ESI pos): 999.5087 [calculated for (M+1)+: 999.5114]. Elemental anal.: calculated (%) for $C_{58}H_{70}N_4O_{11}$: C, 69.72; H, 7.06; N, 5.61; found: C, 69.76; H, 7.36; N, 5.47. HPLC: t=5.3 min, (Ø=1 ml/min; acetonitrile:water/85:15). TLC: Rf: 0.54 (toluene:methanol:ethyl acetate 6:1:1); 0.38 (hexane:THF:triethylamine 5:4:1). $^1$H-RMN: 8.72 (NH-2) 8.90 (NH-3).

Example 32

Preparation of 4-deoxo-3,4-[(2S)-2-spiro(N-butyl-2,6-diphenyl-4-piperidil)-2,5-dihydro-1H-imidazo]rifamycin S (1 RFA-16m)

Following the general procedure of 1RFA (3-16) from the compound 2p shown in Table 2 and the compound (3) shown in Schema 1, the compound of the title was obtained that presents approximately the following data: P.f.: 156-58° C. (desc.). UV (λ=254 nm): 239, 278, 320. HRMS (ESI pos): 999.5102 [calculated for (M+1)+: 999.5114]. TLC: Rf: 0.60 (toluene:methanol:ethyl acetate 6:1:1); 0.20 (hexane:THF:triethylamine 5:4:1). $^1$H-RMN: 8.63 (NH-2) 10.5 (NH-3)

Example 33

Results of the Biological Activity Studies

The studies were carried out using the method of the proportions (reference method) and following the protocol described by the NCCLS (National Comittee for Clinical Laboratory Standards). The culture media was prepared using Middlebrook 7H10 suplemented with about 10% OADC (oleic acid-albumin-dextroxe-catalase). For each compound two (2) inoculums were tested (equivalent to the n°1 of McFarland and a dilution of about 1/100) trying to obtain an ideal inoculum that contains about 100 to about 200 colonies. The plates were incubated in heater at about 37° C., for about 21 days under about 5% to about 10% $CO_2$ atmosphere. In the studies carried out, the behaviour of the compounds analysed demonstrated in vitro a strong antimycobacterialantimycobacterial general activity (minimum inhibitory concentration, MIC<about 0.1 µg/ml) and this activity was found to be more effective than rifampicin-rifabutin in the strain of reference *Mycobacterium tuberculosis* ATCC 37837 that accredits a high grade of resistance to rifampicin. It also emphasized the in vitro behaviour of the compounds in five (5) strains of *Mycobacterium avium-intracellulare* complex analysed, where five strains were sensitive to at least three (3) of the compounds of formula (1) studied. On the contrary, all of them manifested resistance to rifampicin-rifabutin (MIC>about 1 µg/ml). As for the four (4) strains of *Mycobacterium kansasii* all the compounds of formula (1) studied had a similar behaviour to rifampicin-rifabutin.

Table 3 includes the results obtained in the study of biologic activity of the spiropiperidynilrifamycins of general formula (1). s means sensitive, R means resistent and s/R means sensitive to some strains and resistent to others, Each test has been assayed using the compound on several different *Mycobacterium* strains, for example, as in entry 11 of the table, five (5) strains have been used.

If the plate that contains the antibiotic exceeds about 1% of the number of colonies of the control plate (without antibiotic), the microorganism is considered R, in the case of being less than about 1% is considered s.

Entries 1-5 show the results obtained in front of strains of collection (each one resistents to one of the commercial drugs assayed: pyrazinamide PZ, isoniazid IZ, ethambutol EB, rifampicin RI and 2-tiophene hydrazo carboxilic acid TCH), this last drug is used as a control as most *Mycobacterium* are resistent to it. The entries 6-10 show the results obtained in 52 strains assayed, classified in function by resistance observed to commercial drugs. The entries 11 and 12 show the results obtained from 9 atypical *Mycobacterium* strains.

Example 34

Biological Activity Studies in Strains of Multiresistant *Mycobacterium tuberculosis*

Using the same experimental method that was described in Example 33, assays have shown in vitro effectiveness of the compounds of formula (1) exclusively in strains of multiresistant *Mycobacterium tuberculosis*. These strains have been provided by the Microbiological Service of the "Gregorio Marañón" General University Hospital, Madrid; and the Supranational Reference Laboratory Netword of the World Health Organization (Mycrobiological Service, Hospital University Vall d'Hebron, Barcelona). The compounds 1 RFA 3M and 1 RFA 5M, have been tested against multiresistant *Mycobacterium tuberculosis* because they have shown less MIC in the preliminary assays. The obtained results proved a high antimycobacterial activity of the two compounds assayed, much superior to rifampicin and to rifabutin. At a concentration>about 0.5 µg/ml they inhibit growth of more than about 75% of resistant strains to IZ and RI (MIC>about 256 µg/ml).

On the other hand, the rifabutin, at a concentration of about 1 µg/ml shows shows a superior sensitivity of about 14.3% to rifampicin but much lower to 1 RFA 3M and 1 RFA 5M (about 95.2% and about 100% respectively). Table 4 shows collected results of said assays of biological activity of the compounds 1 RFA 3M and 1 RFA 5M. The entry 1 shows the results obtained in four (4) strains resistant to rifampicin. The entry 2 shows the results obtained in seventeen (17) multiresistant strains (Defined here by resistance to resistance to at least isoniazid and rifampicin).).

TABLE 3

Assays of biological activity.

| n° | Strain / Concentration analysed µg/ml | PZ 25 | IZ 0.2 | EB 5 | RI 1 | SM 4 | TCH 1 | RFB 1 | RFA 7M 1 | RFA 4M 1 | RFA 3M 1 | RFA 3m 1 | RFA 5M 1 | RFA 15M 1 | RFA 16M 1 | Control |
|---|---|---|---|---|---|---|---|---|---|---|---|---|---|---|---|---|
| 1 | *Mycobacterium tuberculosis* ATCC 35837 | s | s | s | R | s | R | R | R | s | s | s | s | R | s | Ok |
| 2 | *Mycobacterium tuberculosis* ATCC 35820 | s | s | s | s | R | R | s | s | s | s | s | s | s | s | Ok |
| 3 | *Mycobacterium tuberculosis* ATCC 35838 | s | s | R | s | s | R | s | s | s | s | s | s | s | s | Ok |
| 4 | *Mycobacterium tuberculosis* ATCC 35822 | s | R | s | s | s | R | s | s | s | s | s | s | s | s | Ok |
| 5 | *Mycobacterium tuberculosis* H37 RV | s | s | s | s | s | R | s | s | s | s | s | s | s | s | Ok |
| 6 | *Mycobacterium tuberculosis* | s | s | s | s | s | R | s | s | s | s | s | s | s | s | Ok |

TABLE 3-continued

Assays of biological activity.

| | | | | | | | | Strain | | | | | | | | |
|---|---|---|---|---|---|---|---|---|---|---|---|---|---|---|---|---|
| n° | Concentration analysed μg/ml | PZ 25 | IZ 0.2 | EB 5 | RI 1 | SM 4 | TCH 1 | RFB 1 | RFA 7M 1 | RFA 4M 1 | RFA 3M 1 | RFA 3m 1 | RFA 5M 1 | RFA 15M 1 | RFA 16M 1 | Control |
| 7 | Mycobacterium tuberculosis 38 strains assayed | R | s | s | s | s | R | s | s | s | s | s | s | s | s | Ok |
| 8 | Mycobacterium tuberculosis 8 strains assayed | s | R | s | s | s | R | s | s | s | s | s | s | s | s | Ok |
| 9 | Mycobacterium tuberculosis 2 strains assayed | s | s | s | s | R | R | s | s | s | s | s | s | s | s | Ok |
| 10 | Mycobacterium tuberculosis 3 strains assayed | s | R | s | s | R | R | s | s | s | s | s | s | s | s | Ok |
| 11 | Mycobacterium avium-intracellulare complex 1 strain assayed | R | R | R | R | s/R | R | R | R | s/R | s | s | s | s/R | s/R | Ok |
| 12 | Mycobacterium Kansasii 5 strains assayed | R | R | R | s | R | R | s | s | s | s | s | s | s | s | Ok |

TABLE 4

Assays of biological activity in strains of multiresistant Mycobacterium tuberculosis

| | STRAIN | | | n° (% Sensitivity) | | | | | |
|---|---|---|---|---|---|---|---|---|---|
| | (Concentration | IZ | RI | 1RFA 3M | | | 1RFA 5M | | |
| | analized μg/ml) | (0.2) | (1) | (0.1) | (0.5) | (1) | (0.1) | (0.5) | (1) |
| 1 | Mycobacterium tuberculosis 4 strains assayed | S | R | 1 (25) | 2 (50) | 4 (100) | 1 (25) | 2 (50) | 4 (100) |
| 2 | Mycobacterium tuberculosis multiresistant 17 strains assayed | R | R | 4 (23) | 13 (75) | 16 (94) | 3 (17) | 14 (82) | 17 (100) |

The invention claimed is:

1. A compound of formula (1),

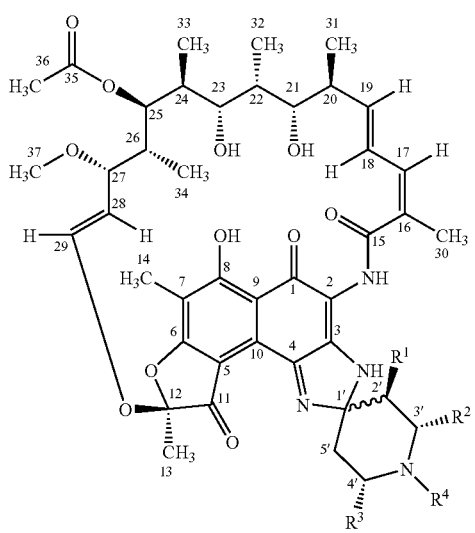

(1)

or a pharmaceutically acceptable salt thereof, wherein:

$R^1$ is a radical selected from hydrogen and $(C_1-C_4)$-alkyl;

$R^2$ is selected from the group consisting of hydroxy-$(C_1-C_4)$-alkyl, phenyl, mono-substituted phenyl and phenyl di-substituted at the positions 3 and 4, the phenyl substituents being selected from the group consisting of halogen, $(C_1-C_4)$-alkyl and $(C_1-C_4)$-alkoxyl;

$R^3$ is selected from the group consisting of phenyl, mono-substituted phenyl and phenyl di-substituted at the positions 3 and 4, the phenyl substitutents being selected from the group consisting of halogen, $(C_1-C_4)$-alkyl and $(C_1-C_4)$-alkoxyl; and $R^4$ is selected from the group consisting of hydrogen, $(C_1-C_4)$-alkyl; allyl, and homoallyl.

2. The compound according to claim 1, wherein when $R^2$ and $R^3$ are mono- or di-substituted phenyl, the substituents of the phenyl are independently selected from halogen and $(C_1-C_4)$-alkoxyl.

3. The compound according to claim 1, wherein the alkoxyl is a methoxyl.

4. The compound according to claim 1, wherein $R^1$ is methyl; $R^2$ is hydroxymethyl; $R^3$ is selected from the group consisting of phenyl and 4-methoxyphenyl; and $R^4$ is hydrogen.

5. The compound according to claim 1, wherein $R^1$ and $R^4$ are hydrogen; and $R^2$ and $R^3$ are selected from the group consisting of phenyl, 4-methoxyphenyl, 4-fluorophenyl, and 2-iodophenyl.

6. The compound according to claim 5, wherein $R^2$ and $R^3$ are identical.

7. The compound according to claim 1, wherein $R^1$ is hydrogen; $R^2$ and $R^3$ are selected from the group consisting of phenyl, 4-methoxyphenyl, 3,4-dimethoxyphenyl, 4-fluorophenyl, 4-chlorophenyl, 2-bromophenyl, 3-bromophenyl, and 2-iodophenyl; and $R^4$ is allyl.

8. The compound according to claim 7, wherein $R^2$ and $R^3$ are identical.

9. The compound according to claim 1, wherein $R^1$ is hydrogen; $R^2$ and $R^3$ are phenyl; and $R^4$ is selected from the group consisting of homoallyl and butyl.

10. A process for the preparation of a compound according to claim 1 comprising reacting, in an suitable solvent, a 3-amino-4-iminorifamycin S of formula (3)

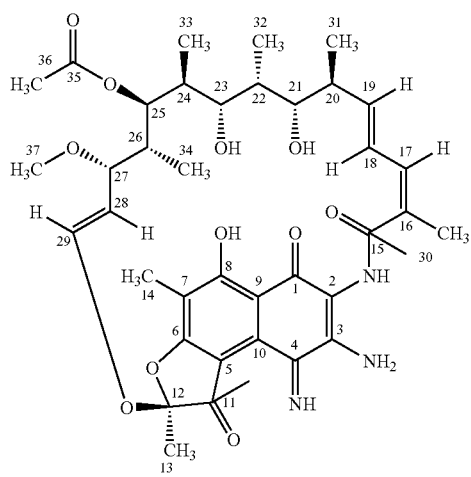

(3)

with a substituted 4-piperidone of formula (2)

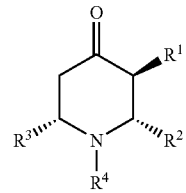

(2)

wherein $R^1$, $R^2$, $R^3$ and $R^4$ are defined as set forth in claim 1.

11. The process according to claim 10, wherein the solvent is a cyclic ether.

12. The process according to claim 11, wherein the cyclic ether is tetrahydrofuran.

13. The process according to claim 10, wherein the reaction is carried out in presence of a base.

14. The process according to claim 13, wherein the base is ammonium acetate.

15. The process according to claim 10, wherein the temperature to which the reaction is carried out is the reflux temperature of the solvent.

16. A method of treatment of a mammal which suffers from a mycobacterial infection that comprises administering to said mammal a therapeutically effective quantity of a compound defined in claim 1, together with suitable quantities of pharmaceutically acceptable excipients or carriers.

17. The method according to claim 16, wherein the mycobacterial infection is produced by a bacterium selected from the group consisting of *Mycobacterium tuberculosis*, *Mycobacterium avium-intracellulare* complex, and *Mycobacterium kansasii*.

18. A pharmaceutical composition for the treatment of mycobacterial infections, which comprises a therapeutically effective quantity of the compound defined in claim 1, together with pharmaceutically acceptable excipients or carriers.

* * * * *